United States Patent [19]
Behl

[11] Patent Number: 5,817,092
[45] Date of Patent: Oct. 6, 1998

[54] APPARATUS, SYSTEM AND METHOD FOR DELIVERING RADIO FREQUENCY ENERGY TO A TREATMENT SITE

[75] Inventor: Robert S. Behl, Palo Alto, Calif.

[73] Assignee: Radio Therapeutics Corporation, Mountain View, Calif.

[21] Appl. No.: 741,763

[22] Filed: Nov. 5, 1996

Related U.S. Application Data

[60] Provisional application No. 60/006,495 Nov. 9, 1995.

[51] Int. Cl.⁶ .................................................. A61B 17/36
[52] U.S. Cl. .................................. 606/41; 606/1; 606/34
[58] Field of Search .................................. 606/41, 42, 1, 606/45–50

[56] References Cited

U.S. PATENT DOCUMENTS

| | | |
|---|---|---|
| 4,449,528 | 5/1984 | Auth et al. . |
| 4,492,231 | 1/1985 | Auth . |
| 4,582,057 | 4/1986 | Auth et al. . |
| 4,691,703 | 9/1987 | Auth et al. . |
| 4,823,791 | 4/1989 | D'Amelio et al. . |
| 4,853,612 | 8/1989 | Kobayashi ............................. 323/354 |
| 5,122,137 | 6/1992 | Lennox . |
| 5,364,393 | 11/1994 | Auth et al. . |
| 5,383,874 | 1/1995 | Jackson et al. . |
| 5,445,635 | 8/1995 | Denen et al. ............................. 606/27 |
| 5,626,575 | 5/1997 | Crenner ..................................... 606/34 |
| 5,651,780 | 7/1997 | Jackson et al. ............................. 606/1 |
| 5,713,896 | 2/1998 | Nardella .................................... 606/50 |
| 5,722,975 | 3/1998 | Edwards et al. .......................... 606/34 |

*Primary Examiner*—Marvin M. Lateef
*Assistant Examiner*—Eleni Mantis Mercader
*Attorney, Agent, or Firm*—Townsend and Townsend and Crew LLP

[57] ABSTRACT

Described are apparatus, systems, and methods for delivering RF energy to a treatment site. The therapeutic system includes a RF power supply and RF therapeutic probe. The probe includes at least one distal electrode and a proximal power supply connector. A control circuit is provided for controlling the amount of RF power supplied to the electrode. The control circuit is formed upon connection of the connector to the power supply.

46 Claims, 6 Drawing Sheets

APPARATUS, SYSTEM AND METHOD FOR DELIVERING RADIO FREQUENCY ENERGY TO A TREATMENT SITE

This application claims the benefit of U.S. Provisional application Ser. No. 60/006,495, filed Nov. 9, 1995, the disclosure of which is incorporated by reference.

BACKGROUND OF THE INVENTION

1. Field of the Invention

The invention relates generally to the field of minimally invasive interventional medical procedures performed by many physician specialties. More particularly, the invention relates to the construction and use of radio frequency (RF) probes and power supplies used in interventional radiology procedures, and particularly for the interface between the probes and the power supplies.

In Interventional Radiology, a wide variety of radiotherapeutic probes may be employed for performing varied therapeutic procedures. Some common radiotherapeutic procedures include the cutting of tissue, the coagulation of tissue (including dessication and fulguration), combinations of cutting and coagulation, and the like. To perform such procedures, the probes are provided with at least one electrode for establishing the flow of RF current through the treatment site.

Such probes can be configured to employ the use of either monopolar or bipolar RF current. For procedures employing monopolar RF current, the probe consists of an active electrode, and a larger passive or return electrode (e.g. a dispersive plate) which is disposed externally or internally on the patient so that RF current can flow from the probe's active electrode to the relatively larger return electrode. With procedures employing bipolar RF current, the probe is provided with at least two similarly sized electrodes between which the RF current is established.

The electrodes employed to establish current flow can be fashioned to have a wide variety of configurations depending on the particular application. Some common electrode shapes include needles, blades, spheres, and the like. One promising electrode configuration is described in copending U.S. application Ser. No. 08/410,344, filed Mar. 24, 1995 (attorney docket no. 63083), the disclosure of which is herein incorporated by reference. Such an electrode configuration comprises a plurality of elongate electrode elements that diverge in a three-dimensional pattern. Such a configuration is particularly useful when treating a specific treatment region within solid tissue. To therapeutically treat the treatment region, the electrodes are introduced to a target site within the treatment region. After reaching the target site, the plurality of electrodes are deployed within the solid tissue, preferably in a configuration which conforms to or encompasses the entire volume of the treatment region. RF current flow is then established between the electrodes (i.e. bipolar) or among the electrodes and a separate return electrode (i.e. monopolar) to uniformly heat and necrose the entire tissue volume being treated.

RF current is supplied to RF probes by a RF power supply. The probe is electrically connected to the power supply by plugging the proximal end of the probe cable into a connector on the power supply.

The particular energy level settings on the power supply and the duration of time for which RF current is supplied to the electrodes can vary widely depending upon the types of electrodes and upon the nature of the procedure. For example, some electrode configurations have a large surface area, thereby increasing the total amount of power that must be delivered to the electrode to effectively coagulate the tissue adjacent to the electrode surface. As physicians become more familiar with each type of probe and with different types of treatment regions, the physician becomes more adept in estimating the level of power that will be needed as well as the duration that such energy should be employed at the treatment region. However, when provided with a probe having a new electrode configuration, the physician may be unfamiliar with how to use the probe, particularly with regard to the amount of RF energy needed and the length of time that the energy is to be supplied to the treatment region. Such unfamiliarity increases the chance of error and potential injury when treating a patient. Further, as the surgeon must learn over time how to use the probe, the cautious user's efficiency will suffer while moving up the learning curve.

When constructing RF probes, there are a number of important design criteria. One important consideration, particularly in single use devices, is manufacturing costs. It is desirable to reduce such costs so that the probes can be competitively marketed. Other important considerations in constructing such probes include the effects of RF emissions caused by the RF current passing through the probes. Such transmission energy may interfere with electrical circuitry in and around the probe. Proper circuit design and proper choice of component values will limit this interference.

Hence, for at least these and other reasons, it would be desirable to provide a system, method and apparatus for delivering RF current to a treatment probe or electrode that would reduce or eliminate the chance of operator error, particularly when the physician is unfamiliar with the apparatus, would be easy to use, thereby reducing or eliminating the learning curve, would be relatively inexpensive, and would generally eliminate or limit undesirable effects of RF emissions on the electronics of the power supply. Further, the RF probe should be easy to interface with its RF power supply.

2. Brief Description of the Background Art

U.S. Pat. No. 5,209,235 describes an ultrasonic imaging catheter assembly having a digital identification circuit used to permit the automatic identification of the catheter assembly.

U.S. Pat. No. 4,292,968 and U.K. Patent Application No. 2,064,178 describe a power supply for a pair of electrodes. The power supply provides a constant current output unless the voltage between the electrodes exceeds a specified amount, whereupon the output is changed to a constant voltage output.

SUMMARY OF THE INVENTION

The invention provides an improved RF probe of the type having at least one distal electrode for delivering RF energy to a treatment site and a proximal connector for connecting the probe to a RF power supply. The improvement comprises providing at least one passive electrical element, such as a resistor, in or associated with the probe so that when the probe is connected to the power supply at least one control circuit is completed. The control circuit is provided to control the amount of RF energy delivered from the electrode to the treatment site. In one aspect, the control circuit may set the duration of the RF energy that is delivered to the treatment site. In another aspect, the control circuit may set the voltage or current and therefore the RF power that is supplied to the electrode. In still a further aspect, the probe may optionally be configured to simultaneously control both the RF power and treatment duration.

Conveniently, both circuits may be constructed by incorporating two distinct resistors in the same probe connector. In this way, the amount of RF energy supplied to the treatment site is controlled by the probe in a fail-safe manner rather than by manual adjustment of the power supply. The need for a physician to adjust a timer or a power level setting on the power supply, or to estimate the time for which RF current should be supplied to a treatment site (and risk that these parameters will be improperly chosen) is thus eliminated or greatly reduced. In a preferable aspect, the passive electrical element comprises a resistor in the connector. In this way, the length of time or the particular power level can be tailored to a particular size and configuration of probe by the specific resistance of its incorporated resistor.

The probe will usually comprise a probe body having a proximal end, a distal end, a connecting cable extending from the proximal end of the probe body, and a connector plug secured to the proximal end of the connecting cable. Usually, the probe body, connector cable, and connector plug will be permanently attached to each other to form an integral assembly (i.e., the components are not intended to be interchangeable). In some cases, however, the components of the assembly could be replaceable and reconfigurable, although it is not preferred since it increases the complexity of the system and the likelihood of making an error.

In a particularly preferable aspect, the probe includes first and second control pins extending from the connector. The passive electrical element is preferably incorporated into the connector and extends between the pins so that when the pins are inserted into the power supply, a timing circuit containing the passive element is completed. The timing circuit is designed to be at least partially protected against the RF current flowing through the probe.

In one preferable embodiment, the connector further includes a third pin and at least a second passive element extending between the third pin and one of the first or the second pins, with the second passive element having a resistance that is different from the resistance of the first passive element. In this way, the connector can be connected to the power supply to place either the first or the second resistor into the timing circuit. By providing different resistance values to each of the passive elements, the length of the timing cycle can be varied depending upon which of the passive elements are placed into the timing circuit (i.e., the time is selected by adjusting the orientation of the probe connector relative to a connector receptacle on the power supply). In another exemplary aspect, the connector is triangular in geometry, with the three possible control pins being disposed about the corners of the triangle. In this way, the connector can be rotated to be connected to the power supply in one of three different orientations, each of which selectively determines a unique combination of passive elements.

The connector is provided with a single power lead or a pair of power leads depending upon whether the probe is for monopolar or bipolar use. The power lead(s) serves as a current-carrying conductor so that RF current can be delivered to the probe.

In still a further aspect, the probe includes a visual label indicating the duration or RF power level that will be supplied by the electrode upon appropriate orientation of the probe connector to the power supply. In this way, a physician can visually determine the duration or power level of RF energy that will be supplied to the electrode.

The invention further provides a radiotherapeutic system having a RF power supply and a RF therapeutic probe. The probe includes at least one distal electrode and a proximal power supply connector. The system further includes a timing circuit for controlling the duration of RF energy supplied to the electrode. The timing circuit is completed by connection of the probe connector to the power supply. In one aspect, the timing circuit comprises an RC circuit having in parallel a resistor and a capacitor, with the resistor located within the probe and the capacitor located within the power supply. In this way, the duration of the RF energy supplied to the electrode is based on the selection of the probe which includes the resistor. Preferably, the power supply will be provided with timing circuitry including an integrated circuit timer which in combination with the probe connector resistor controls the duration of RF current that is supplied to the electrode.

In a preferable aspect, the probe comprises a probe body having a proximal end, a distal end, a connecting cable extending from the proximal end of the probe body, and a connector plug secured to the proximal end of the connecting cable. The connector cable is preferably integrally or permanently connected to both the probe body and the connector plug. Optionally, the cable can be configured to be removably attached to the probe body, but in some manner keyed so that the proper connector plug is matched with the appropriate probe body.

In one aspect, the connector preferably includes first and second control circuit pins, with the resistor embedded within the body of the connector and wired between the two pins. The capacitor (or alternative timing circuitry) is included in the power supply so that when the pins of the connector are inserted into the power supply the resistor is placed in electrical communication with the capacitor to complete the timing circuit. A switch is further provided for manually initiating the timing cycle after connection of the probe to the power supply. When the switch is closed, RF current flows though the probe for the duration as selected by the resistor.

The probe, or more likely the probe connector, will preferably include a visual label that indicates the duration of RF energy that will be supplied to the electrode based upon the particular resistor within that connector.

In an alternative aspect, the power supply is intentionally set to provide power for a fixed interval and is further provided with a means for adjusting the amount of RF power supplied to the electrode. In this way, the fixed resistor within each probe connector may be employed to determine the specific level of RF energy delivered to the probe for the given time period. A smaller probe can thus be fabricated with a connector resistor value that will cause the power supply to deliver less power than delivered to a large probe.

In yet another alternative, the connector may include two sets of pins. One set will determine duration of RF power provided to that particular probe by completing the resistive portion of the power supply timing circuit. The other set of pins and their associated resistor complete and control the power supply output level control circuit, thus determining the level of RF power delivered to the probe. Of necessity, the four pins are preferably asymmetrical in location, or are included within a "keyed" connector to ensure proper orientation.

The probe can be configured to supply either monopolar or bipolar RF current to the treatment site. For monopolar current, the connector plug is provided with a single RF power lead. The power lead is inserted with the connector into the power supply and serves as a RF current-carrying conductor so that RF current can be delivered to the probe and electrode from the power supply. For bipolar current, the probe includes at least two distal electrodes and the connector plug includes a pair of RF power leads.

The invention provides a method for treating a tissue region with RF current. According to the method, a probe is provided having at least one distal electrode and a proximal power supply connector. The probe is attached to a RF power supply by inserting the connector into a mating receptacle in the power supply, and the electrode is introduced to the treatment region. RF current flow is then established from the electrode. The duration of the RF current flow provided by the electrode and/or the level of RF power delivered to the probe is controlled with a control circuit. In one aspect, the control circuit is a timing circuit, such as an RC circuit that is formed by placing a resistor in the connector in series with a capacitor in the power supply upon connection of the probe to the power supply. The timing circuit is employed to send a signal to enable the delivery of RF current to the probe for a specified period of time.

In one aspect, a voltage drop across the capacitor is detected so that the supply of RF current to the electrode will be terminated when the detected voltage is less than a predetermined level. When the predetermined level of voltage drops below this threshold, a solid state switch or other device interrupts the supply of RF current supplied to the probe. In this manner, RF current is supplied to the electrode for a known time as dictated by the resistance of the resistor in the probe (which in turn controls the rate of the voltage drop across the capacitor). Hence, by varying the resistance of the resistor the duration of the RF current supplied to the electrode can be precisely controlled. In another aspect, the capacitor is charged by the power supply prior to providing RF current to the electrode.

Current flow can be established between one electrode at the distal end of the probe and a common return electrode in a monopolar fashion. Alternatively, the probe can be provided with at least two electrodes at the distal end so that current flow can be established between the two electrodes in a bipolar fashion.

In a further aspect of the method, the control circuit is a power level control circuit for controlling the amount of power that is delivered to the electrode. The power level control circuit is formed by placing a passive electrical element in the probe connector in parallel with an amplifier within the power supply.

DESCRIPTION OF THE PREFERRED EMBODIMENT

Figure 1:
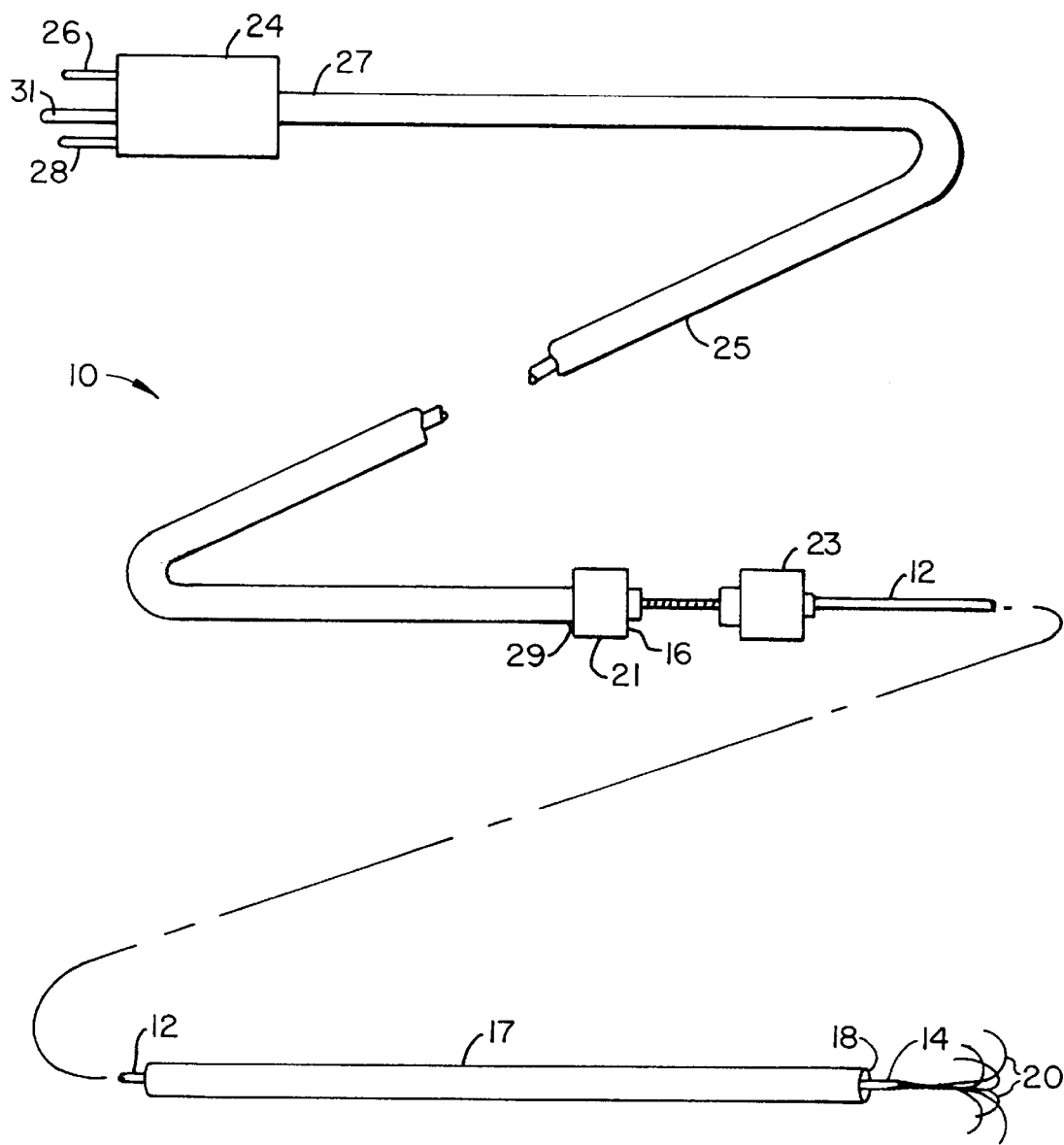
FIG. 1 illustrates an exemplary embodiment of a RF probe assembly according to the present invention.

According to the present invention, the amount of RF energy supplied to a treatment region is controlled. The RF energy is supplied to the treatment region by a RF probe. The present invention employs at least one element of the probe connector to dictate the length of time for which RF power is supplied to the probe, to dictate the level of RF power supplied to the probe, or both. By controlling the supply of RF power in a manner specific to an individual probe type or size, a physician is provided with a way to safely and efficiently treat a desired region, even when being unfamiliar with the electrical requirements of a particular configuration of the probe. The chance of error in over or under treating a patient is greatly reduced. The time required in learning how to effectively operate the probe is also reduced or eliminated.

In one aspect, the invention provides such features by employing a timing circuit that is controlled by connection of the probe to a RF power supply. The timing circuit is preferably created by providing a passive element in the probe which completes the timing circuit upon connection to the power supply. In this alternative, the length of the timing cycle is controlled by the resistance of the passive element. In this manner, a wide variety of probes can be provided, with the duration of the supply of RF current provided to each probe being controlled by the resistance of the passive element(s) within each probe connector.

One particular advantage of such a timing circuit is that the timing can be tailored to each type of probe electrode configuration and according to the particular amount of energy required for a given procedure. Thus, the same nominal probe configuration can be specifically provided for a variety of procedures by merely offering a variety of resistances of the passive element within the probe connector. For most procedures, the power supply will be configured to supply a fixed or preprogrammed level of voltage for the time that the current is supplied. Preferably, the output characteristics of the power supply will be matched with the impedance of the target tissue to ensure the energy output of the power supply is highly predictable. Optionally, the power supply can be provided with a variety of power level settings so that the same probe can be used at different energy levels. In an alternative construction, the power setting may be determined by a second passive element within the connector which forms a power level control circuit upon connection of the probe to the power supply.

The probes of the present invention can be constructed in a variety of ways, but will usually always include at least one distal electrode, a proximal power supply connector, and at least one passive electrical element so that the timing and/or power control circuit can be created when the probe is connected to the power supply. Usually, the probe will include a probe body having a distal end and a proximal end, with the electrode located at the distal end, a connector cable fixed or removably attached to the proximal end of the probe body, and a power supply connector plug attached to the proximal end of the cable. With such a configuration, the passive electrical element will optimally be formed within the connector plug, but can be included anywhere on or associated with the probe.

The probes are each preferably marked with a visual marker that indicates the amount of time for which current will be supplied to the probe's electrode upon connection of the probe to the power supply and subsequent actuation. Optionally, the probe can be provided with a second visual marker to indicate a particular power level setting for which the probe is intended to be operated. In such an option, the power supply can be adjusted to the setting indicated by the second visual marker on the probe to properly set the power output level of the power supply. In a further option, the power output is determined by a second passive element within the connector.

The probe of the invention is preferably disposable so that it can be discarded after use. One particular advantage of this probe is that the passive element which will be discarded with the probe is very inexpensive and is not environmentally hazardous. Further, the incorporation of the passive element into a probe contained portion of the timing circuit allows the power supply to be constructed without the use of a computer or micro-processor, thereby reducing the manufacturing costs of the related hardware. Another exemplary aspect of the probe is that the timing circuit components contained within the connector are protected by design or shielding from the RF current passing through the probe.

The probe of the invention can be provided with a wide variety of electrode configurations, such as needle electrodes, blade electrodes, spherical coagulation electrodes, conization electrodes, loop electrodes, and the like. As described in greater detail hereinafter, one exemplary electrode configuration includes a plurality of elongate electrode wires that are disposed in a three-dimensional pattern as described in U.S. patent application Ser. No. 08/410,344, filed Mar. 24, 1995, the disclosure of which has previously been incorporated herein by reference. The electrodes employed by probes of the invention can be configured for use with either monopolar or bipolar current.

In another aspect, each probe can alternatively be provided with more than one passive element, with each passive element having a different resistance value. Since the length of power delivery is based on the resistance of the passive element, the user will have the choice of operating the probe over several predetermined time intervals depending upon which passive element is introduced into the timing circuit. In a preferable aspect, the passive elements are provided in a power supply connector on the proximal end of the probe so that, depending upon the orientation of the connector when inserted into the power supply, a different passive element will be introduced into the timing circuit.

Referring now to FIG. 1, an exemplary embodiment of a RF probe assembly 10 will be described. The probe assembly 10 includes an elongate probe body 12 having a distal end 14 and a proximal end 16. Disposed over the probe body 12 is an elongate sheath 17 having a central lumen 18 extending therethrough. At the distal end 14 of probe body 12 are a plurality of tissue-penetrating electrodes 20. The electrodes 20 comprise electrically conductive wires extending through probe body 12, which in turn passes through the central lumen 18. The electrodes 20 are slidable within the probe body 12 so that the electrodes 20 can be retracted within the probe body 12 during insertion into a patient. Access to the patient is accomplished through sheath 17 (previously placed). When the distal end 14 reaches a treatment region within the patient, the electrodes 20 are advanced from the distal end 14 and through tissue at the treatment region. Advancement of the electrodes 20 proceeds by proximally translating the electrodes 20 relative to the probe body 12. Moving hubs 21 and 23 together or apart correspondingly translates the electrodes 20 relative to the probe body 12. With the electrodes inserted into the desired tissue, RF current is supplied to the electrodes 20 to treat the region.

Figure 2:
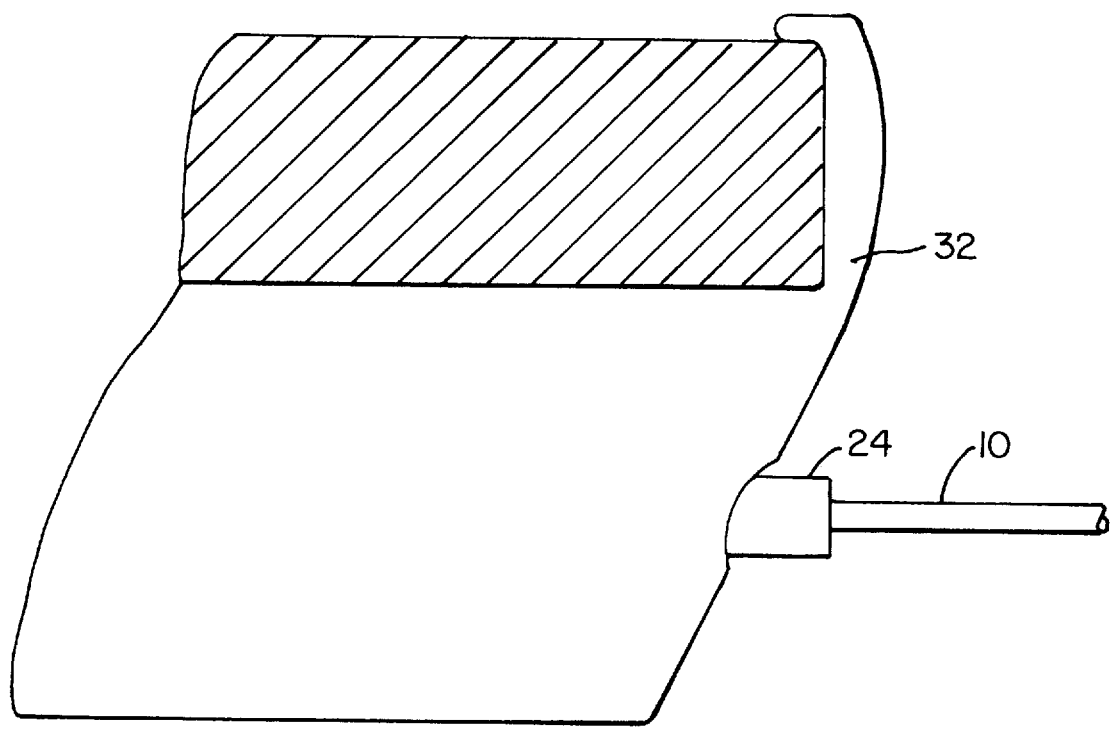
FIG. 2 is a side view of a proximal end of the probe of FIG. 1 connected to a RF power supply.

The probe assembly 10 further includes a connector cable 25 having a proximal end 27 and a distal end 29. The probe body 12 is connected to the cable 25 at the distal end 29. This connection can be a removable connection, or preferably, the cable 25 is permanently attached and integrally formed with the probe body 12. As RF current is supplied through the cable 25, it passes through the probe 12 and the electrodes 20. Connected to the proximal end 27 of the cable 25 is a power supply connector plug 24. Extending proximally from the connector 24 are pins 26, 28, and 30 (with pin 30 being behind pin 28). As described in greater detail hereinafter, extending between at least some of the pins 26, 28, and 30 is a passive element(s) (not shown), such as a resistor, used to complete a timing circuit when the probe assembly 10 is connected to a RF power supply 32 as shown in FIG. 2. The connector 24 further includes a power lead 31. The power lead 31 is a RF current-carrying pin that is used to deliver RF current from the power supply 32, through the cable 25, and to the probe 12 and electrodes 20.

Figure 3:
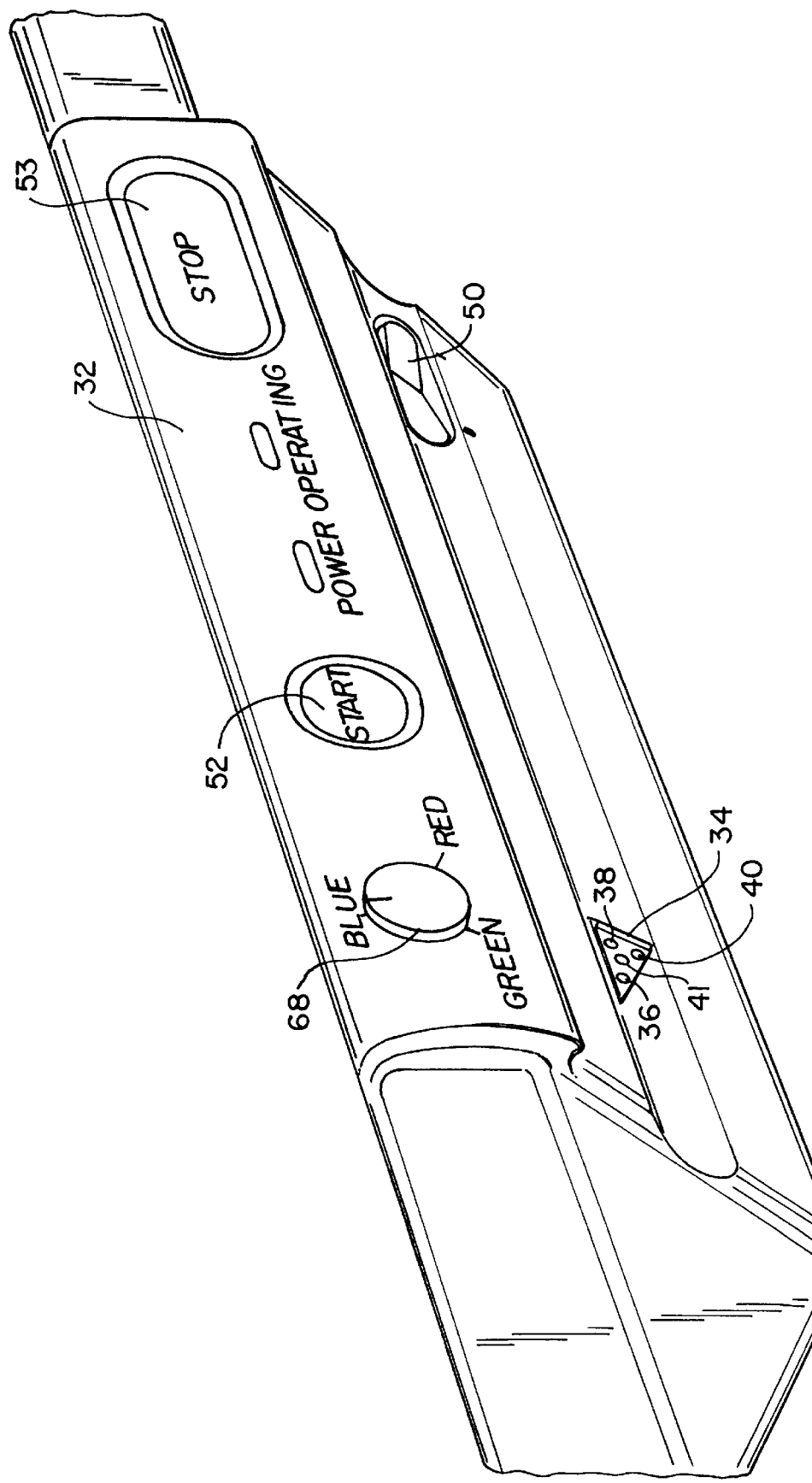
FIG. 3 illustrates a front view of the power supply of FIG. 2 according to the present invention.
Figure 4:
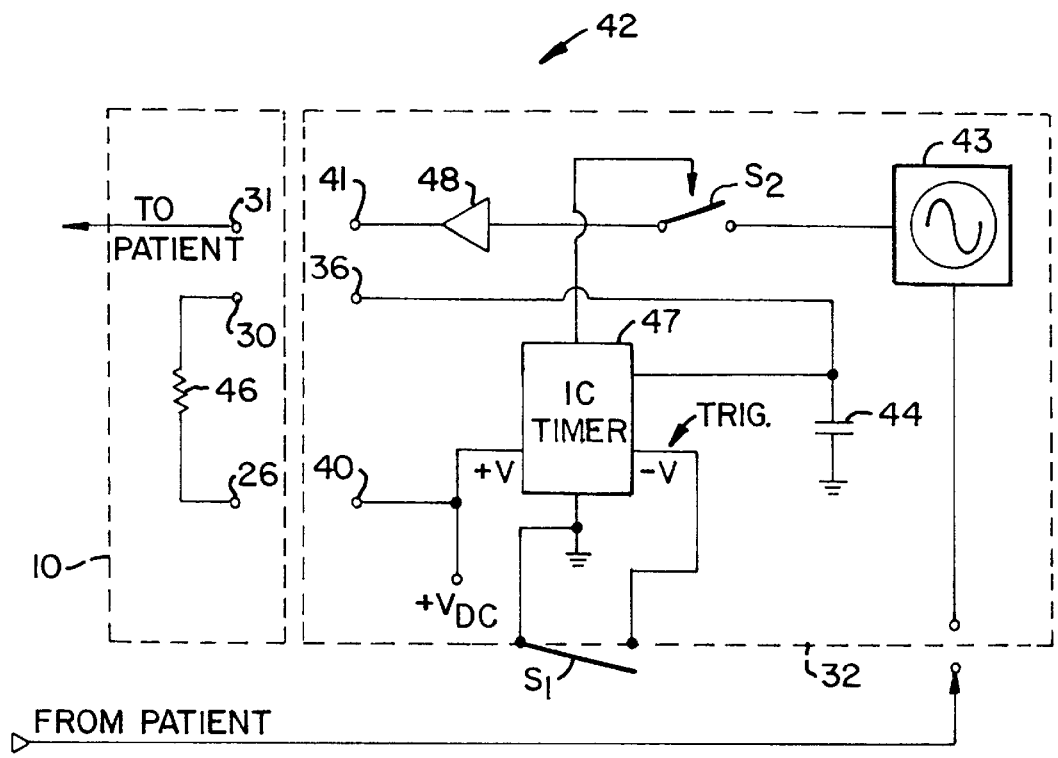
FIG. 4 is a schematic of a timing circuit for controlling the duration of RF energy supplied to a probe according to the present invention.

Referring to FIGS. 3 and 4, construction of the power supply 32 will be described in greater detail. When the probe 10 (not shown) is inserted into an outlet 34, the pins 26, 28, 30 are received into corresponding sockets 36, 38, and 40, while power lead 31 is received into a socket 41. Two of the sockets, e.g. sockets 36 and 40, are connected to a timing circuit 42 (see FIG. 4). As illustrated in FIG. 4, the timing circuit 42 is a RC circuit having a capacitor 44, a resistor 46, and an integrated circuit (IC) timer 47. The resistor 46 is part of the probe 10 and extends between two of the pins 26, 28, or 30, while the capacitor 44 and the IC timer 47 are part of the RF power supply 32. The resistor 46 can be held between any of the pins 26, 28, 30, but for convenience of discussion will be described as extending between pins 26 and 30. In this manner, when the pins 26 and 30 are inserted into the sockets 36 and 40, the resistor 46 is connected to the IC timer 47 to form the timing circuit 42.

The output of the IC timer 47 can then be used to control the supply of RF current supplied by the power source 32 (via a RF oscillator 43) to the probe assembly 10. In this way, the duration of power supplied to the probe assembly 10 is dictated by the resistance of the resistor 46 which is held within the probe assembly 10.

The IC timer 47 in the timing circuit 42 can be actuated in a variety of ways, one way being to provide switch S1 as shown in FIG. 4. Switch S1 is controlled by a start button 52 on the power supply 32. An on/off switch 50 is further provided on the power supply 32 so that power may be supplied to the RF oscillator 43. When a physician is ready to perform a procedure, the probe 10 is connected to the power supply 32, the on/off switch 50 is turned to the "on" position, and the start button 52 is pressed to start the IC timer 47. The timer 47 initiates the delivery of RF current to the probe 10 by sending a signal to close a switch S2 so that RF current may be delivered to the probe 10 from a power amplifier 48. The delivery interval is determined by the resistance of the resistor 46 in the probe assembly 10. RF current may then be again supplied to the probe 10 by again closing the switch S1. Additionally, a stop button 53 will be provided on the power supply 32 so that RF current may be terminated at any time.

Figure 5:
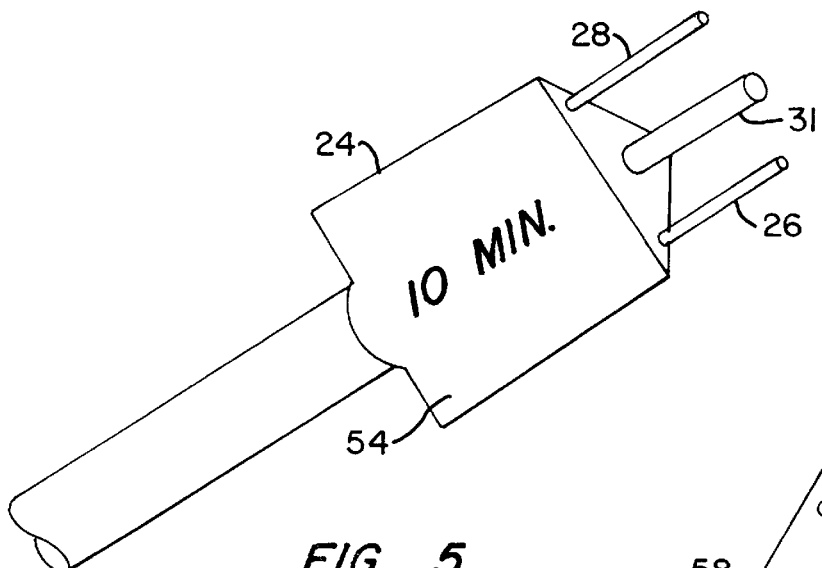
FIG. 5 is a perspective view of the proximal end of the probe of FIG. 1.
Figure 6:
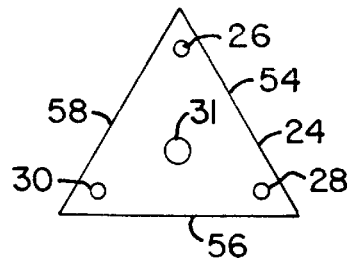
FIG. 6 is an end view of the proximal end of the probe of FIG. 1.

Referring to FIGS. 5 and 6 (with FIG. 6 being an end view of FIG. 5), the connector 24 will be described in greater detail. The connector 24 is triangular in geometry with the pins 26, 28, 30 disposed near the corners of the triangle. As described in greater detail hereinafter, configuring the connector 24 with a triangular geometry allows for the connector 24 to be inserted into the outlet 34 in any one of three different orientations. The triangular geometry of the connector 24 provides the connector with three faces 54, 56, and 58. Any two of the three pins 26, 28, and 30 and the resistive value between them will complete the timing circuit.

As shown in FIG. 5, the face 54 is marked with the time length for which the probe 10 will be actuated corresponding to the resistor 46 extending between the pins 26 and 28. Hence, by orienting the face 54 in a unique position relative to the power supply 32, the duration of RF current supplied to the probe 10 as determined by the resistor, can easily be visualized. For example, if pins 26 and 28 engage sockets 36 and 38, the connector face 54 will be oriented upward. Face 54 will indicate the energy delivery time determined by resistor 46. Hence, as shown in FIG. 5, if face 54 were facing upward when connected to the power supply 32, the probe 10 will be actuated for a time period of 10 minutes when the start button 52 is pressed.

Figure 7:
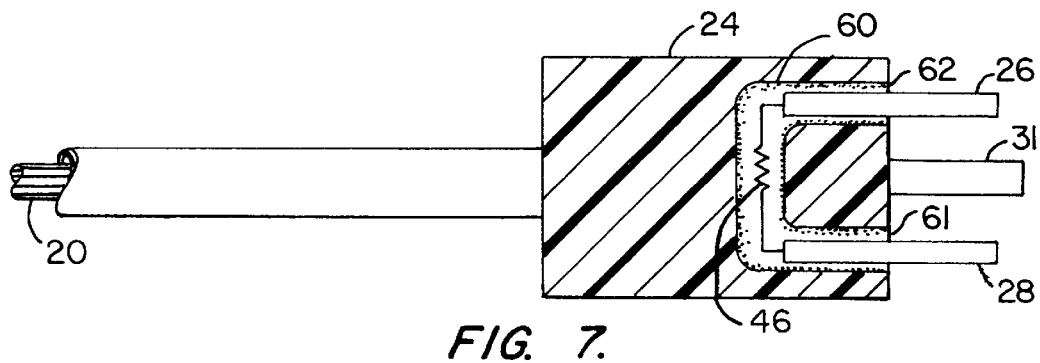
FIG. 7 is a cutaway side view of the proximal end of the probe of FIG. 1.

Referring to FIG. 7, shielding of the pins 26, 28, 30, and associated connector circuitry will be described. Each of the pins having a resistor extending therebetween are provided with a RF shield 60, such as shielding typically used with coaxial cable, to prevent interference from the RF current passing through the closely adjacent power lead 31. The shield 60 is grounded to the power supply 32 by a common ground lead or coaxial connector (not shown) at proximal ends 61 and 62 of the shield 60.

Figure 8:
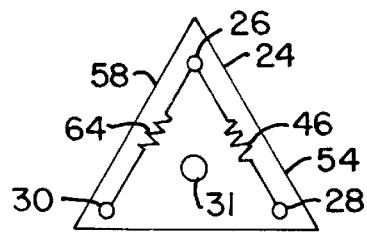
FIG. 8 is a schematic view of one embodiment of a circuit design for the probe of FIG. 1 according to the present invention.

Referring to FIG. 8, the connector 24 can alternatively be provided with a second resistor 64 in addition to the resistor 46. The resistor 64 extends between the pins 26 and 30 and has a resistance that is different from the resistor 46. In this way, the probe 10 can be operated for two different time periods depending upon which resistor 46 or 64 is placed in the timing circuit 42. For example, resistor 46 may be placed into the timing circuit by inserting the pins 26 and 28 into sockets 36 and 38 (FIG. 3). To place the resistor 64 in the timing circuit 42, connector 24 is rotated 120 degrees and pins 30 and 26 are respectively placed into sockets 36 and 38.

Figure 9:
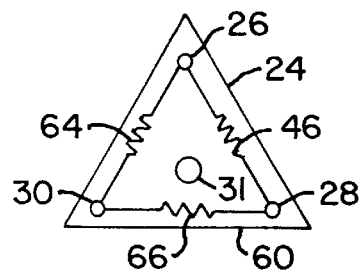
FIG. 9 is a schematic view of an alternative circuit design for the probe of FIG. 1.

As illustrated in FIG. 9, the connector 24 can alternatively be provided with a third resistor 66 extending between the pins 28 and 30. To place the resistor 66 in the timing circuit 42, the pins 28 and 30 are respectively inserted into sockets 36 and 38 to place the face 60 in a upward position. When all three pins are interconnected, the total equivalent resistance is a function of both the resistor value between the two pins and the series resistance between the other two pins. The equivalent resistance value between pins 28 and 30 is different from the equivalent values between the other pin combinations so that the probe 10 can be operated for one of three different time periods.

Referring back to FIG. 3, the power supply 32 can optionally be provided with a power control switch 68 (not shown) to vary the amount of RF current supplied to the probe 10. The different power level settings are indicated visually on the power supply 32. The particular settings can be indicated on the power supply 32 in a variety of ways, such as showing actual power levels in watts or by providing colored labels, such as blue, red, and green. When color coding is used, each probe connector is preferably provided in a different color corresponding to the power level at which the probe is intended to be operated. The switch 68 can then be turned to the color coded power setting which matches the color of the probe. Further, the length of time that the power is supplied to the probe can be controlled by the orientation of the probe within the outlet 34 as previously described.

Figure 10:
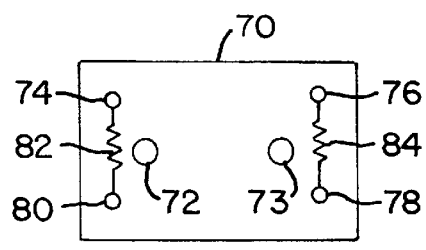
FIG. 10 is a schematic illustration of an alternative power supply connector for the probe of FIG. 1 having resistors extending vertically between the pairs of pins.
Figure 11:
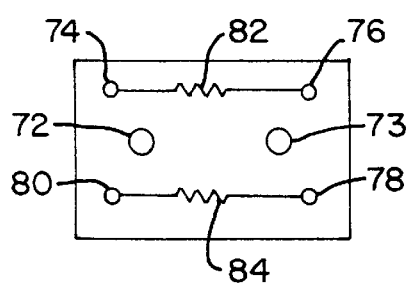
FIG. 11 is a schematic view of an alternative embodiment of the connector of FIG. 10 having resistors extending horizontally between two pairs of pins.

Referring to FIG. 10, an alternative embodiment of a power supply connector 70 will be described. The power supply connector 70 includes two power leads 72, 73 that allow the probe 10 to be operated in a bipolar manner. The connector 70 further includes four pins 74, 76, 78, and 80. Extending between the pins 74 and 80 is a resistor 82. When the connector 70 is used with the power supply 32, the power supply will include an outlet adapted to receive the two leads 72, 73 and the pins 74, 76, 78, and 80 in a manner similar to the outlet 34 of FIG. 3. When the pins 74 and 80 are inserted into the outlet in a predetermined orientation, the resistor 82 is placed in the timing circuit 42. The power supply connector 70 can further include a second resistor 84 between the pins 76 and 78, with the resistor 84 having a different resistance than the resistor 82. To place the resistor 84 in the timing circuit 42, the connector 70 is rotated 180 degrees so that pins 76, 78 and resistor 84 replace pins 74, 80, and resistor 82 in the timing circuit. Instead of placing the resistor 82 between the pins 74 and 80 and the resistor 84 between the pins 76 and 78, the resistor 82 can alternatively be placed between the pins 74 and 76 and the resistor 84 between the pins 80 and 78 as shown in FIG. 11. Timing could also be changed by rotating the connector.

Figure 12:
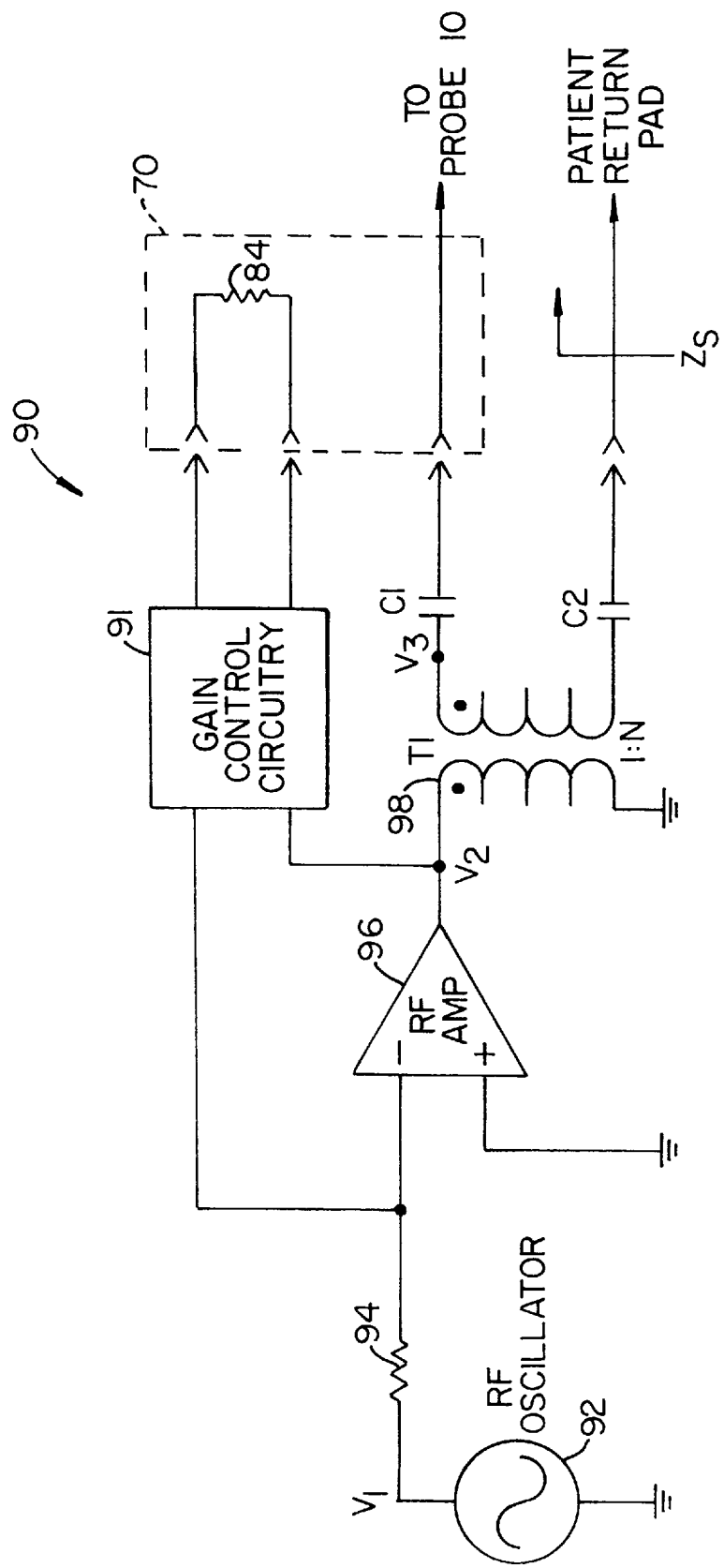
FIG. 12 is a schematic of a power level control circuit according to the present invention.

Any connector configuration containing more than one set of pins and included resistor may be further employed to control both power level and time of application simultaneously. For example, in FIG. 11 resistor 82 may complete the timing circuit of the power supply 32, while the resistor 84 may complete a functionally similar power level control circuit, thereby simultaneously determining both levels by plugging the connector pins into the power supply. In this specific case, the connector would be keyed in some manner to assume the proper orientation. Shown in FIG. 12 is an exemplary schematic of a power level control circuit 90 employed to control the amount of power supplied to the probe 10 using the resistor 84 of connector plug 70. The control circuit 90 includes a RF oscillator 92 and RF amplifier 96 for providing RF current. The value of the resistor 84 in connector 70 dictates the amount of amplification provided by gain control circuit 91 acting through the amplifier 96. The RF current exiting the amplifier 96 passes through a transformer 98 and to the probe 10.

Although the foregoing invention has been described in detail by way of illustration and example, for purposes of clarity of understanding, it will be obvious that certain changes and modifications may be practiced within the scope of the appended claims.

What is claimed is:

1. An improved RF probe assembly of the type having at least one distal electrode for delivering RF energy to a treatment site and a proximal connector adapted for connection to a RF power supply, the improvement comprising:

a passive electrical element for completing a control circuit within the power supply when the connector is connected to the power supply, said control circuit directly and automatcally controlling the amount of RF energy delivered to the treatment region based on said passive electrical element.

2. The probe assembly of claim 1, wherein the control circuit comprises a timer for controlling the duration of RF energy delivered to the treatment region.

3. The probe assembly of claim 2, further comprising a visual label on the connector indicating the duration of RF energy that will be supplied to the electrode upon connection of the connector to the power supply.

4. The probe assembly of claim 1, wherein the control circuit comprises a power level regulator for controlling the level of RF power supplied to the electrode.

5. The probe assembly of claim 1, wherein the passive electrical element comprises a resistor in the connector.

6. The probe assembly of claim 1, further comprising at least a first pin and a second pin extending from the connector, with the passive element extending between the pins, and wherein the pins are adapted to be inserted into the power supply to complete the control circuit when inserted therein.

7. The probe assembly of claim 6, wherein the connector includes a third pin, and wherein at least a second passive element extends between the third pin and one of the first or the second pins, and wherein the second passive element has a resistance that is different from the resistance of the first passive element, whereby the connector is adapted to be connected to the power supply to place either the first or the second passive element in the control circuit.

8. The probe assembly of claim 7, wherein the connector is triangular in geometry, and wherein the pins are disposed near the corners of the triangle.

9. The probe assembly of claim 1, wherein the passive element within the connector is at least partially surrounded by a RF shield.

10. The probe assembly of claim 1, wherein the connector includes a single RF power lead.

11. The probe assembly of claim 1, further comprising at least two distal electrodes, and wherein the connector includes a pair of RF power leads.

12. The probe assembly of claim 1, further comprising a probe body having a proximal end and a distal end, with the electrode located at the distal end, and a cable connecting the connector to the proximal end of the probe body, and wherein the passive electrical element is disposed in the connector.

13. The probe assembly of claim 12, wherein the cable is fixedly attached to both the connector and the proximal end of the probe body.

14. The probe assembly of claim 12, wherein the cable is removably attached to the proximal end of the probe body.

15. The probe assembly of claim 12, wherein the probe body is disposable.

16. A radiotherapeutic system comprising:
   a RF power supply;
   a RF therapeutic probe assembly having at least one distal electrode and a proximal power supply connector; and
   a timing circuit which controls the duration of RF energy supplied to the electrode, the timing circuit being formed upon connection of the connector to the power supply.

17. The system of claim 16, wherein the timing circuit comprises electrical components in the power supply and at least a first pin and a second pin in the connector, with a capacitor extending between the two pins, and wherein insertion of the two pins into the power supply places the resistor in electrical communication with the electrical components to complete the timing circuit.

18. The system of claim 16, wherein the timing circuit comprises electrical components in the power supply and at least a first pin and a second pin in the connector, with a resistor extending between the two pins, and wherein insertion of the two pins into the power supply places the resistor in electrical communication with the electrical components to complete the timing circuit.

19. The system of claim 18, wherein at least one of the electrical components comprises an integrated circuit timer in parallel with a capacitor.

20. The system of claim 18, further comprising a switch for manually closing the timing circuit after connection of the probe to the power supply.

21. The system of claim 18, wherein the connector includes a third pin, and wherein at least a second resistor extends between the third pin and one of the first or the second pins, and wherein the second resistor has a resistance that is different from the resistance of the first resistor, whereby the connector can be connected to the power supply to place either the first or the second resistor in the timing circuit.

22. The system of claim 21, wherein the connector is triangular in geometry, and wherein the pins are disposed near the corners of the triangle.

23. The system of claim 18, wherein the pins are at least partially surrounded by a RF shield.

24. The system of claim 18, further comprising a power level control circuit for controlling the amount of RF power delivered to the electrode, the power level control circuit being formed upon connection of the connector to the power supply.

25. The system of claim 24, wherein the power level control circuit comprises a passive electrical element in the power supply connector that controls the gain of a RF amplifier in the power supply when the connector is connected to the power supply.

26. The system of claim 25, wherein the probe assembly further comprises a probe body having a proximal end and a distal end, with the electrode located at the distal end, and a cable connecting the proximal connector to the proximal end of the probe body, and wherein the passive electrical element is disposed in the connector.

27. The system of claim 26, wherein the probe body is disposable.

28. The system of claim 26, wherein the cable is removably attached to the proximal end of the probe body.

29. The system of claim 26, wherein the cable is fixedly attached to both the connector and the proximal end of the probe body.

30. The system of claim 16, wherein the connector includes a single RF power pin.

31. The system of claim 16, wherein the probe includes at least two electrodes, and wherein the connector includes a pair of RF power pins.

32. The system of claim 16, wherein the probe includes a visual label indicating the duration of RF energy that will be supplied to the electrode upon connection of the probe to the power supply.

33. The system of claim 32, wherein the visual label is on the connector.

34. The system of claim 16, further comprising means on the power supply for adjusting the amount of RF energy supplied to the electrode.

35. A method for treating region with RF current, comprising:
   providing a probe assembly having at least one distal electrode and a proximal power supply connector;

attaching the probe to a RF power supply by inserting the connector into the power supply, wherein connection of the connector to the power supply completes a control circuit;

introducing the electrode to the treatment region;

establishing RF current flow from the electrode; and controlling the amount of RF energy delivered to the treatment region with at least one passive electrical element within the connector.

36. The method of claim 35, wherein the controlling step comprises forming a timing circuit upon attachment of the probe assembly to the RF power supply to control the duration of RF current flow.

37. The method of claim 36, wherein the timing circuit comprises an RC circuit that is formed by placing in parallel a resistor with a capacitor upon connection of the probe assembly to the power supply.

38. The method of claim 37, further comprising detecting a voltage drop across the capacitor and stopping the supply of RF current to the electrode when the detected voltage is less than a predetermined amount.

39. The method of claim 37, wherein the capacitor is within the connector.

40. The method of claim 37, wherein the resistor is within the connector.

41. The method of claim 35, wherein the probe assembly includes at least two electrodes at the distal end, and wherein the establishing step further comprises establishing current flow between the at least two electrodes.

42. The method of claim 35, wherein the establishing step further comprises establishing current flow between the electrode and a common electrode.

43. The method of claim 35, wherein the control circuit comprises a timing circuit which controls the duration of RF current flow.

44. The method of claim 35, wherein the control circuit comprises a power level control circuit which controls the level of RF power delivered to the electrode.

45. The method of claim 44, wherein the power level control circuit includes a power amplifier.

46. The method of claim 35, wherein the control circuit controls both the duration of RF current flow to the electrode and the level of RF power delivered to the electrode.

* * * * *